United States Patent
Higuchi et al.

(10) Patent No.: US 9,599,600 B2
(45) Date of Patent: Mar. 21, 2017

(54) SENSOR CONTROL APPARATUS AND GAS DETECTION SYSTEM

(71) Applicant: NGK SPARK PLUG CO., LTD., Nagoya-shi, Aichi (JP)

(72) Inventors: Yuzo Higuchi, Komaki (JP); Tomonori Uemura, Komaki (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 198 days.

(21) Appl. No.: 14/565,015

(22) Filed: Dec. 9, 2014

(65) Prior Publication Data

US 2015/0177209 A1   Jun. 25, 2015

(30) Foreign Application Priority Data

Dec. 24, 2013   (JP) ................................ 2013-265468

(51) Int. Cl.
*G01N 27/407*   (2006.01)
*G01N 33/00*   (2006.01)
*G01N 27/41*   (2006.01)
*G01N 27/406*   (2006.01)

(52) U.S. Cl.
CPC ....... *G01N 33/0073* (2013.01); *G01N 27/407* (2013.01); *G01N 27/4065* (2013.01); *G01N 27/41* (2013.01)

(58) Field of Classification Search
CPC ..... G01N 27/41; G01N 27/409; G01N 27/407
See application file for complete search history.

(56) References Cited

U.S. PATENT DOCUMENTS 4,665,874 A * 5/1987 Kawanabe ......... G01N 27/4065
                                                                    123/679

FOREIGN PATENT DOCUMENTS

JP      2008-008667 A    1/2008

* cited by examiner

*Primary Examiner* — Alexander Noguerola
(74) *Attorney, Agent, or Firm* — Stites & Harbison, PLLC; Jeffrey A. Haeberlin; James R. Hayne

(57) ABSTRACT

A sensor control apparatus controls a gas sensor by means of digital control and restrains a decrease in accuracy of pump current control. A gas detection system includes such a sensor control apparatus. The sensor control apparatus includes a reference voltage generation section, and can change the maximum current range of pump current Ip in the current DA conversion section. The sensor control apparatus can set the maximum current range of the pump current Ip to a proper range in accordance with the type or characteristic of a gas sensor to be controlled. Namely, in the case where a gas sensor has a small sensor maximum current, the maximum current range of the current DA conversion section is changed to a range determined in consideration of the sensor maximum current of the gas sensor, which restrains a decrease in the accuracy in controlling the pump current Ip.

6 Claims, 9 Drawing Sheets

(a) Resolution when 11.5 mA range is set: 2.8 µA
(b) Resolution when 4.0 mA range is set: 0.98 µA

SENSOR CONTROL APPARATUS AND GAS DETECTION SYSTEM

BACKGROUND OF THE INVENTION

Field of the Invention

The present invention relates to a sensor control apparatus which controls a gas sensor having an oxygen pump cell for pumping oxygen in or out in accordance with pump current, and to a gas detection system which includes such a gas sensor and such a sensor control apparatus.

Description of Related Art

Conventionally, there has been known a gas detection system which includes a gas sensor having an oxygen pump cell for pumping oxygen in or out in accordance with pump current, and a sensor control apparatus for controlling the gas sensor.

One example of such a gas sensor is a linear A/F sensor which performs pumping in or out of oxygen contained in a gas under measurement by using an oxygen pump cell, and detects the oxygen concentration of the gas under measurement on the basis of the pump current supplied such that the oxygen concentration of the gas under measurement becomes equal to a predetermined target concentration. Another example of such a gas sensor is an NOx sensor which detects the NOx concentration of a gas under measurement.

The sensor control apparatus must have various computation functions for controlling the pump current of such a gas sensor, and also must meet demand for reduction in the size of the apparatus. In order to satisfy these requirements, there has been used a sensor control apparatus which employs a digital control section in place of an analog circuit for performing various types of controls.

Such a sensor control apparatus including a digital control section has a digital-to-analog conversion section for converting a digital value (computation result) to an analog current. One example of the digital-to-analog conversion section is a current DAC (digital-to-analog converter) which inputs and outputs current as an analog value.

Such a digital-to-analog conversion section allows the sensor control apparatus to control the pump current (analog value) supplied to the pump cell of the gas sensor while computing the pump current by means of digital control at the digital control section.

Such a digital control section can be reduced in size as compared with an analog circuit, and can make an operation of changing control constants easier as compared with an analog circuit. Therefore, a sensor control apparatus employing such a digital control section can be easily adapted to control of gas sensors of a larger number of types and control of gas sensors having various characteristics.

RELATED ART DOCUMENTS

Patent Document 1 is Japanese Patent Application Laid-Open (kokai) No. 2008-008667

BRIEF SUMMARY OF THE INVENTION

However, a sensor control apparatus which can cope with gas sensors of a larger number of types (or various characteristics) through employment of a digital control section has a possibility that, when it controls a gas sensor whose maximum current (sensor maximum current) is small, the accuracy of pump current control decreases due to the influence of a quantization error at a digital-to-analog conversion section.

Namely, in the case where the range of maximum current which can be supplied by the digital-to-analog conversion section is fixed, in the sensor control apparatus employing a digital control section, the maximum current range within which pump current can be supplied from the apparatus (i.e., the maximum current range within which pump current can be supplied from the digital-to-analog conversion section) is set in consideration of the maximum current of a sensor which is the largest in sensor maximum current among gas sensors of various types (or various characteristics).

Such a sensor control apparatus has the following problem. When the sensor control apparatus controls a gas sensor whose maximum current (sensor maximum current) is small, it supplies the pump current only within a range narrower than the maximum range of the digital-to-analog conversion section. Therefore, the accuracy in controlling the pump current decreases.

For example, in the case where the maximum current range of a 13-bit digital-to-analog conversion section is set for a gas sensor whose maximum current (sensor maximum current) is ±11.5 mA, the effective number of bits of the digital-to-analog conversion section decreases to 11 to 12 bits when the sensor control apparatus controls a gas sensor whose maximum current (sensor maximum current) is ±4.0 mA.

FIG. 10 shows an explanatory graph representing the characteristic of a 13-bit digital-to-analog conversion section (current DAC) for the case where the maximum current range of the 13-bit digital-to-analog conversion section (current DAC) is set to ±11.5 mA. As shown in FIG. 10, when the digital-to-analog conversion section outputs pump current within a range of ±4.0 mA, of the width W1 of the maximum range (13 bits) of the digital-to-analog conversion section, only a partial width W2 which is equal to or less than a half of the width W1 (about one third of the width W1) can be used. Therefore, the effective number of bits decreases to 11 to 12 bits.

Namely, in the case where the maximum current range within which the digital-to-analog conversion section can supply the pump current is fixed, as the sensor maximum current of the gas sensor decreases, the ratio of the current value per bit to the sensor maximum current of the gas sensor increases. Therefore, accurate control of the pump current becomes difficult, and the accuracy in controlling the pump current decreases.

In view of the forgoing problem, an object of the present invention is to provide a sensor control apparatus which controls a gas sensor by means of digital control and which can restrain a decrease in the accuracy in controlling the pump current. Another object of the present invention is to provide a gas detection system including such a sensor control apparatus.

A sensor control apparatus of the present invention is adapted to control a gas sensor having an oxygen pump cell for pumping oxygen in or out in accordance with a pump current. The sensor control apparatus comprises a pump current computation section, a digital-to-analog conversion section, and a maximum current range change section. The pump current compensation section computes, by means of digital control, a digital signal corresponding to a pump current supplied to the oxygen pump cell, and provides the digital signal. The digital-to-analog conversion section generates the pump current supplied to the oxygen pump cell, on the basis of the digital signal representing a result of computation by the pump current computation section. The maximum current range change section changes a maximum current range of the pump current which can be generated by the digital-to-analog conversion section.

The sensor control apparatus includes the maximum current range change section, and the maximum current range change section is configured to change the maximum current range of the pump current which can be generated by the digital-to-analog conversion section. Therefore, the sensor control apparatus can change the maximum current range of the pump current to a proper range in accordance with the type or characteristic of a gas sensor to be controlled.

Namely, in the case where a gas sensor whose sensor maximum current is small is controlled, the maximum current range of the digital-to-analog conversion section is changed to a range determined in consideration of the sensor maximum current of the gas sensor, whereby a decrease in the accuracy in controlling the pump current can be restrained.

Therefore, according to the sensor control apparatus of the present invention, a decrease in the accuracy in controlling the pump current can be restrained when the gas sensor is controlled by means of digital control.

Notably, the pump current supplied to the oxygen pump cell by the digital-to-analog conversion section is not unidirectional but bidirectional (forward direction and reverse direction). Therefore, the operation of the oxygen pump cell can be switched between an oxygen pumping in operation and an oxygen pumping out operation in accordance with the supply (flow) direction (forward direction, reverse direction) of the pump current.

The sensor control apparatus of the present invention may be configured as follows. The digital-to-analog conversion section is configured such that the maximum current range changes with a reference voltage externally supplied, and the maximum current range change section changes the maximum current range by changing the reference voltage. In other words, the maximum current range change section generates the reference voltage; and the digital-to-analog conversion section is configured such that the maximum current range changes with the reference voltage.

The sensor control apparatus having such a configuration can arbitrarily change the maximum current range of the digital-to-analog conversion section by changing the reference voltage by the maximum current range change section.

The sensor control apparatus of the present invention may be further configured as follows. The digital-to-analog conversion section may include a variable resistance section whose electrical resistance is variable (i.e., the variable resistance section has variable electrical resistance), and generates, as the pump current, a current produced as a result of application of the reference voltage to the variable resistance section.

Since the variable resistance section is provided in the digital-to-analog conversion section, the pump current can be generated as a current produced as a result of application of the reference voltage to the variable resistance section.

The sensor control apparatus of the present invention may also be configured as follows. The maximum current range change section may change the maximum current range on the basis of sensor information determined in accordance with a characteristic or type of the gas sensor, and the sensor control apparatus may comprise a storage section for storing the sensor information.

A proper maximum current range of the pump current corresponding to the characteristic or type of the gas sensor can be set by determining the sensor information in accordance with the characteristic or type of the gas sensor.

Also, through employment of a configuration of storing the sensor information in the storage section, it becomes possible to change the information stored in the storage section (sensor information) in accordance with the gas sensor to be controlled.

As a result, the sensor control apparatus of the present invention can cope with gas sensors of various types or gas sensors having various characteristics, and can restrain a decrease in the accuracy in controlling the pump current.

The sensor control apparatus of the present invention may still further be configured as follows. The gas sensor may include a detection cell which generates an electromotive force corresponding to a specific component contained in a gas under measurement. Then, the sensor control apparatus may include an analog-to-digital conversion section for converting an analog value of the electromotive force to a digital value, and the pump current computation section may compute the pump current on the basis of the digital value of the electromotive force.

The gas sensor which includes a detection cell in addition to an oxygen pump cell has a higher gas detection accuracy as compared with a gas sensor which includes the oxygen pump cell only.

The sensor control apparatus which includes an analog-to-digital conversion section and in which the pump current computation section computes the pump current on the basis of electromotive force can control a gas sensor including an oxygen pump cell and a detection cell.

Therefore, the sensor control apparatus of the preset invention can control a gas sensor including an oxygen pump cell and a detection cell, and can improve the accuracy of gas detection.

A gas detection system of the present invention comprises the above-described sensor control apparatus and a gas sensor having an oxygen pump cell for pumping oxygen in or out in accordance with pump current.

Since this gas detection system includes the above-described sensor control apparatus, a decrease in the accuracy in controlling the pump current can be restrained as in the case of the above-described sensor control apparatus. Specifically, in the case where a gas sensor whose sensor maximum current is small is controlled, the maximum current range of the digital-to-analog conversion section is changed to a range determined in consideration of the sensor maximum current of the gas sensor, whereby a decrease in the accuracy in controlling the pump current can be restrained.

Therefore, according to the gas detection system of the present invention, a decrease in the accuracy in controlling the pump current can be restrained when the gas sensor is controlled by means of digital control.

BRIEF DESCRIPTION OF THE DRAWINGS

Illustrative aspects of the invention will be described in detail with reference to the following figures wherein.

DETAILED DESCRIPTION OF EXEMPLARY EMBODIMENTS OF THE INVENTION

Embodiments of the present invention will now be described with reference to the drawings.

Notably, the present invention is not limited to the following embodiments, and various other forms may be employed without departing from the technical scope of the present invention.

A. First Embodiment
1-1. Overall Configuration

Figure 1:
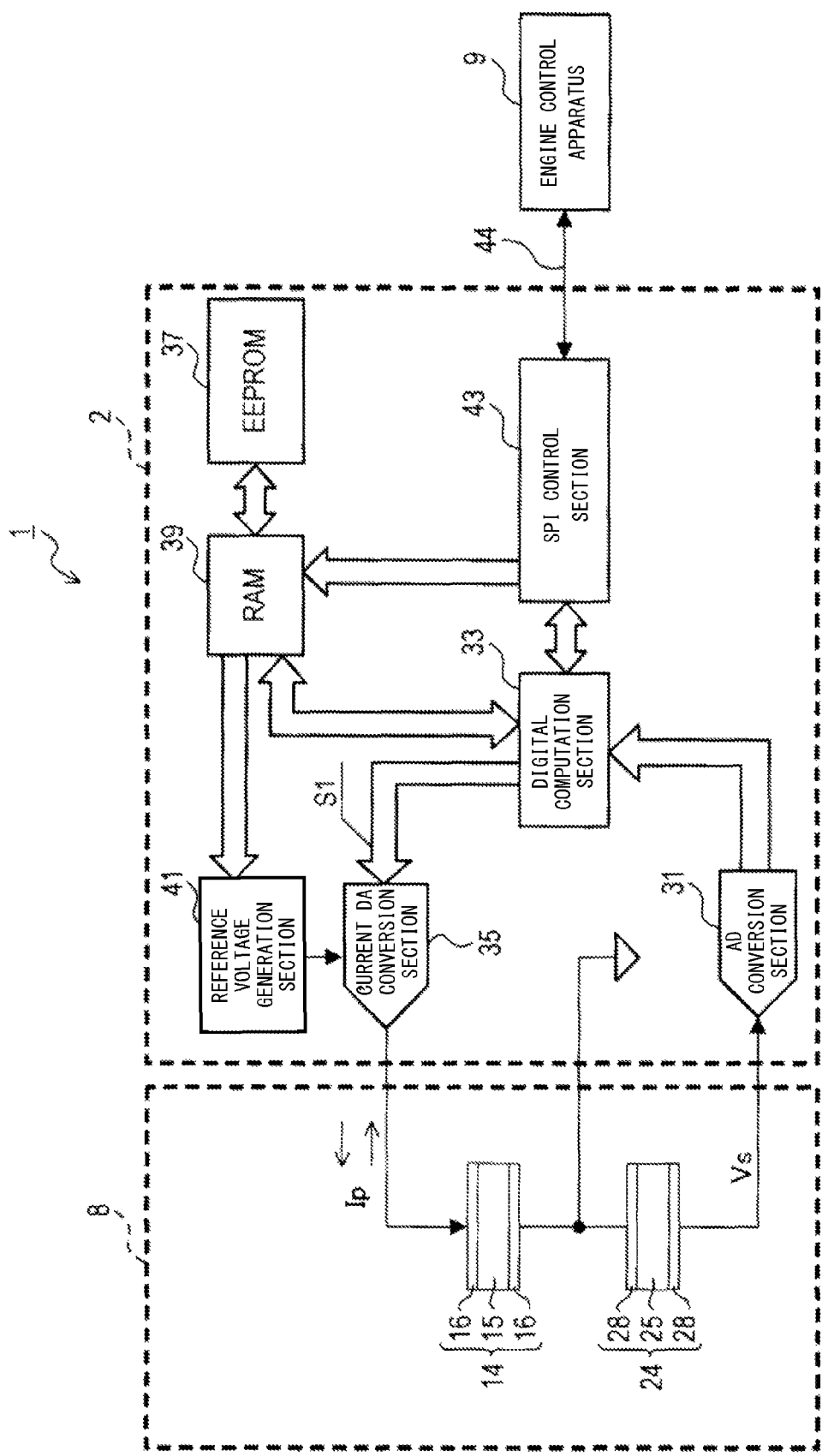
FIG. 1 is an overall diagram of a gas detection system 1.

FIG. 1 is an overall diagram of a gas detection system 1 which is an embodiment to which the present invention is applied.

The gas detection system 1 is used for, for example, detection of a specific gas (oxygen in the present embodiment) contained in exhaust gas discharged from an internal combustion engine.

The gas detection system 1 includes a gas sensor 8 for detecting oxygen, and a sensor control apparatus 2 for controlling the gas sensor 8. The gas detection system 1 notifies an engine control apparatus 9 of the detected oxygen concentration.

The engine control apparatus 9 is a microcontroller which executes various types of control processes for controlling the internal combustion engine. The engine control apparatus 9 performs, as one of the various types of control processes, an air-fuel-ratio control for the internal combustion engine by using the oxygen concentration detected by the gas detection system 1.

The gas sensor 8 is provided on an exhaust pipe of the internal combustion engine (engine), and detects the oxygen concentration of exhaust gas over a wide range. The gas sensor 8 is also called a linear A/F sensor. The gas sensor 8 is composed of a pump cell 14 and an electromotive force cell 24.

The pump cell 14 includes an oxygen ion-conductive solid electrolyte member 15 formed of partially stabilized zirconia ($ZrO_2$), and a pair of porous electrodes 16 mainly formed of platinum and provided on the front and back surfaces, respectively, of the solid electrolyte member 15. The electromotive force cell 24 includes an oxygen ion-conductive solid electrolyte member 25 formed of partially stabilized zirconia ($ZrO_2$), and a pair of porous electrodes 28 mainly formed of platinum and provided on the front and back surfaces, respectively, of the solid electrolyte member 25.

The gas sensor 8 has a measurement chamber (not shown) provided inside the gas sensor 8 to be located between the pump cell 14 and the electromotive force cell 24. A gas under measurement (exhaust gas in the present embodiment) is introduced into the measurement chamber through a porous diffusion layer (not shown).

The gas sensor 8 operates as follows. The electromotive force cell 24 generates an electromotive force (detection voltage Vs) corresponding to the oxygen concentration of the measurement chamber (in other words, the oxygen concentration of the gas under measurement introduced into the measurement chamber through the porous diffusion layer). Specifically, a detection voltage Vs corresponding to the difference in oxygen concentration between the porous electrode 28 on the front surface and the porous electrode 28 on the back surface is generated at the electromotive force cell 24.

The oxygen contained in the gas under measurement within the measurement chamber is pumped out or oxygen is pumped into the measurement chamber, through use of the pump cell 14, such that the detection voltage Vs of the electromotive force cell 24 becomes equal to a predetermined reference value (for example, about 450 mV). Specifically, a pump current Ip is caused to flow between the porous electrode 16 on the front surface of the pump cell 14 and the porous electrode 16 on the back surface of the pump cell 14 so as to pump out oxygen within the measurement chamber or pump oxygen into the measurement chamber, to thereby adjust the oxygen concentration of the measurement chamber.

Namely, the gas sensor 8 is used for an application in which the oxygen concentration of the gas under measurement is detected on the basis of the pump current Ip caused to flow through the pump cell 14 such that the oxygen concentration of the measurement chamber becomes equal to a predetermined target concentration (for example, a concentration corresponding to the stoichiometric A/F ratio).

The sensor control apparatus 2 drives and controls the gas sensor 8 so as to detect the oxygen concentration of the exhaust gas, and reports the detected oxygen concentration to the engine control apparatus 9 via an SPI communication line 44.

The sensor control apparatus 2 includes an AD conversion section 31 (analog-to-digital conversion section 31), a digital computation section 33, a current DA conversion section 35 (current digital-to-analog conversion section 35), an EEPROM 37, a RAM 39, a reference voltage generation section 41, and an SPI control section 43.

The AD conversion section 31 converts an analog value of the detection voltage Vs generated at the electromotive force cell 24 of the gas sensor 8 to a digital value, and sends the digital value of the detection voltage Vs to the digital computation section 33. Notably, the detection voltage Vs generated across the electromotive force cell 24 changes with the oxygen concentration of the measurement chamber.

The digital computation section 33 is a central processing unit (CPU) which executes various types of computation/control processes. As one of the computation/control processes, the digital computation section 33 performs a pump current control process of controlling the pump current Ip supplied to the pump cell 14 such that the detection voltage Vs of the electromotive force cell 24 becomes equal to a target control voltage (450 mV in the present embodiment).

Specifically, the digital computation section 33, which executes the pump current control process, performs PID computation on the basis of a difference (deviation) ΔVs between the target control voltage (450 mV) and the detection voltage Vs of the electromotive force cell 24, and controls the pump current Ip supplied to the pump cell 14 by the current DA conversion section 35 such that the deviation Aby approaches zero (in other words, the detection voltage Vs approaches the target control voltage).

Notably, the digital computation section 33 transmits to the current DA conversion section 35 a DAC control signal S1 containing information regarding the pump current Ip. The DAC control signal S1 is a digital signal which contains information regarding the magnitude and supply (flow) direction (forward direction, reverse direction) of the pump current Ip.

The current DA conversion section 35 performs DA conversion on the basis of the DAC control signal S1 which contains the information regarding the pump current Ip computed by the digital computation section 33, and supplies the pump current Ip to the pump cell 14. Notably, the details of the current DA conversion section 35 will be described later.

The EEPROM 37 is a storage section for storing the contents of the computation/control processes, various parameters used for the computation/control processes, etc.

The EEPROM 37 stores sensor information which includes at least information regarding a reference voltage Vref corresponding to the maximum current range of the pump current Ip and information used for correction of a variation produced in the course of manufacture. This sensor information is determined in accordance with the type or characteristic of the gas sensor 8 to be controlled. In the present embodiment, the sensor information is stored in the EEPROM 37 when the sensor control apparatus 2 is manufactured, and may be rewritten in the field after shipment.

The RAM 39 is a storage section for temporarily storing control data, etc., used for the various types of computation/control processes.

The reference voltage generation section 41 generates the reference voltage Vref on the basis of "information regarding the reference voltage Vref" temporarily stored in the RAM 39 and supplies the generated reference voltage Vref to the current DA conversion section 35.

Notably, the "information regarding the reference voltage Vref" temporarily stored in the RAM 39 is also used in the pump current control process performed by the digital computation section 33. That is, in the pump current control process, with the maximum current value in the maximum current range corresponding to the reference voltage Vref being set as a current value corresponding to the maximum value of the DAC control signal S1, the value of the DAC control signal S1 corresponding to the computation result (the current value of the pump current Ip) is computed on the basis of the ratio between the computation result (the current value of the pump current Ip) and the maximum current range.

When this DAC control signal S1 is sent to the current DA conversion section 35, the current DA conversion section 35 supplies to the pump cell 14 the pump current Ip determined on the basis of the DAC control signal S1.

The SPI control section 43 controls data communications performed through a serial peripheral interface, and controls transmission of data to the engine control apparatus 9 through the SPI communication line 44 and reception of data from the engine control apparatus 9 through the SPI communication line 44.

1-2. Current Da Conversion Section 35

Next, the configuration of the current DA conversion section 35 will be described.

Figure 2:
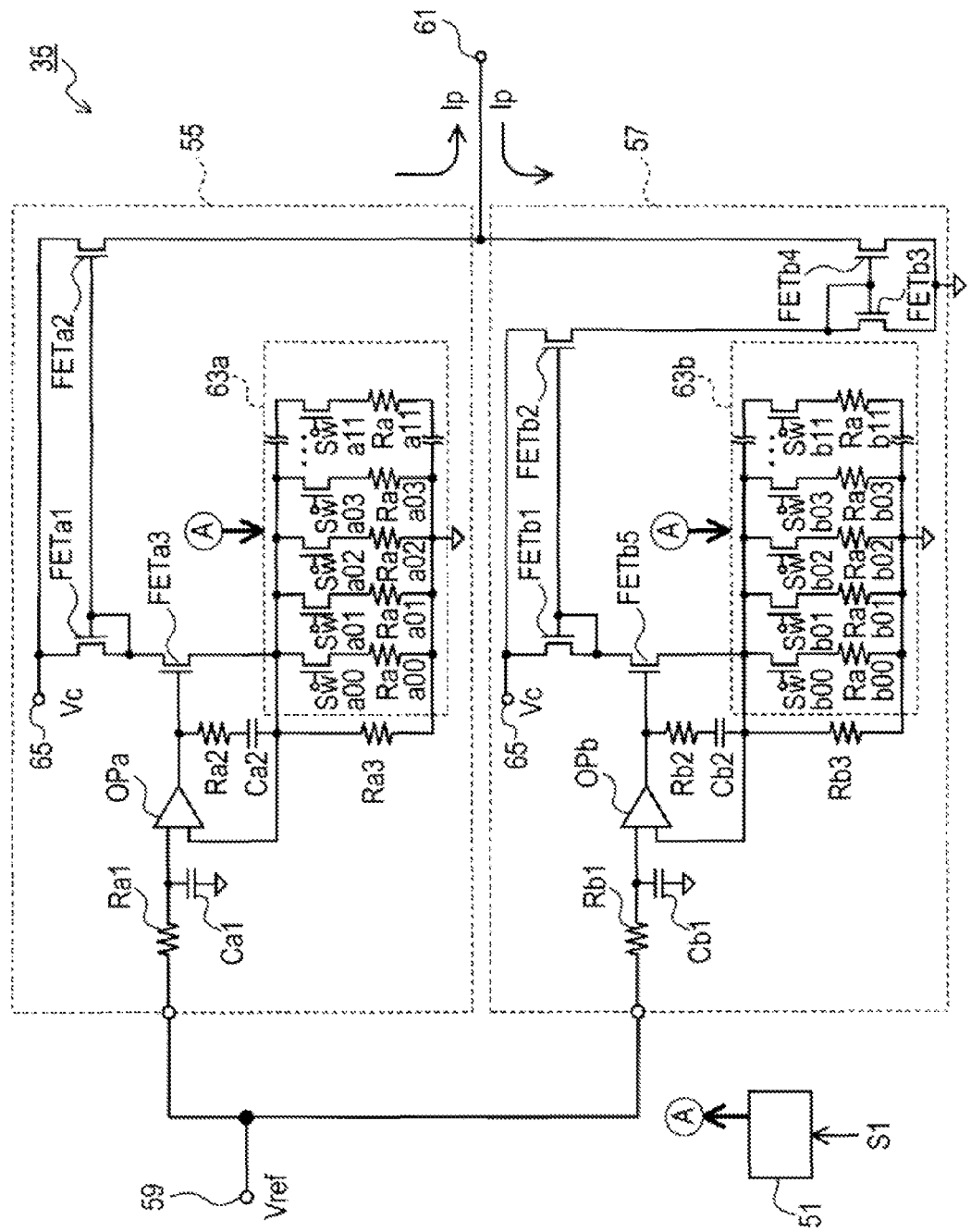
FIG. 2 is an overall diagram of a current DA conversion section 35.

FIG. 2 is an overall diagram of the current DA conversion section 35.

The current DA conversion section 35 includes a digital signal control section 51, a forward direction energization section 55, a reverse direction energization section 57, a reference voltage terminal 59, a pump current terminal 61, and a circuit power supply terminal 65.

On the basis of the DAC control signal S1 from the digital computation section 33, the digital signal control section 51 sets the states (open (OFF) or closed (ON) states) of switching elements Swa00 to Swa11 of the forward direction energization section 55 to be described later, the states (open (OFF) or closed (ON) states) of switching elements Swb00 to Swb11 of the reverse direction energization section 57 to be described later, an energization current value used in the forward direction energization section 55, and an energization current value used in the reverse direction energization section 57.

Notably, the DAC control signal S1 is data of 13 bits, 1 bit of which is used as information regarding the supply direction of the pump current Ip and 12 bits of which are used as information regarding the current value of the pump current Ip.

The reference voltage terminal 59 is electrically connected to the forward direction energization section 55 and the reverse direction energization section 57. Notably, the reference voltage terminal 59 is connected to the reference voltage generation section 41 (not shown in FIG. 2), and the reference voltage Vref is supplied from the reference voltage generation section 41.

Namely, the reference voltage Vref supplied from the reference voltage generation section 41 is supplied to the forward direction energization section 55 and the reverse direction energization section 57 through the reference voltage terminal 59.

The circuit power supply terminal 65 is connected to a circuit power supply (not shown) for supplying a predetermined power supply voltage Vc, and partially constitutes an electric power supply path for supplying the power supply voltage Vc from the circuit power supply to the forward direction energization section 55 and the reverse direction energization section 57.

The forward direction energization section 55 includes an operational amplifier OPa, a variable resistor circuit 63a, a plurality of field effect transistors FETa1, FETa2, FETa3, a plurality of resistor elements Ra1, Ra2, Ra3, a plurality of capacitors Ca1, Ca2, etc.

The variable resistor circuit 63a includes 12 resistor elements Raa00 to Raa11, and 12 switching elements Swa00 to Swa11. In FIG. 2, some of the resistor elements Raa00 to Raa11 and some of the switching element Swa00 to Swa11 are not shown.

The resistances of the 12 resistor elements Raa00 to Raa11 are adjusted by changing their lengths, widths, or numbers of sub elements forming the respective resistor elements such that the ratio of a reference resistance Rref to the resistance of the resistor element Raa(n) becomes "the nth power of 2." For example, in the case where the resistance of the resistor element Raa00 is "Rref/(the 0th power of 2)," the resistance of the resistor element Raa01 is "Rref/(the first power of 2)," the resistance of the resistor element Raa02 is "Rref/(the second power of 2)," and the resistance of the resistor element Raa11 is "Rref/(the eleventh power of 2)."

The states (open (OFF) states or closed (ON) states) of the 12 switching elements Swa00 to Swa11 are set on the basis of the DAC control signal S1. Namely the variable resistor circuit 63a is configured to change the changeover states of the forward direction energization section 55 and the reverse direction energization section 57 and the electrical resistance of the entire circuit on the basis of the DAC control signal S1.

When, on the basis of the setting of the digital signal control section 51, some or all of the switching elements Swa00 to Swa11 of the forward direction energization section 55 are brought into their closed states (ON states) and all of the switching elements Swb00 to Swb11 of the reverse direction energization section 57 are brought into their open states (OFF states) (hereinafter, this state will be referred to as a first state), in the forward direction energization section 55, the reference voltage Vref is applied to the variable resistor circuit 63a as a result of feedback control performed by the operational amplifier OPa.

In the forward direction energization section 55, the field effect transistors FETa1 and FETa2 form a current mirror circuit, and the two field effect transistors are of the same size in the present embodiment. Therefore, a current determined by the reference voltage Vref and the electrical resistance of the variable resistor circuit 63a flows through the field effect transistor FETa1, and a current of the same magnitude flows through the field effect transistor FETa2. The current flowing through the field effect transistor FETa2 in this manner is supplied to the pump cell 14 through the pump current terminal 61 as a pump current Ip of a direction toward the pump cell 14 (forward direction).

Namely, in the case where the first state is established on the basis of the setting of the digital signal control section 51, the pump current Ip of the forward direction is supplied to the pump cell 14 by the forward direction energization section 55.

Meanwhile, when, on the basis of the setting of the digital signal control section 51, all of the switching elements Swa00 to Swa11 of the forward direction energization section 55 are brought into their open states (OFF states) and some or all of the switching elements Swb00 to Swb11 of the reverse direction energization section 57 are brought into their closed states (ON states) (hereinafter, this state will be referred to as a second state), the voltage applied to the variable resistor circuit 63a as a result of feedback control performed by the operational amplifier OPa becomes 0 V, and no current flows through the variable resistor circuit 63a. Namely, in the case where the second state is established on the basis of the setting of the digital signal control section 51, the supply of the pump current Ip by the forward direction energization section 55 is not performed.

The reverse direction energization section 57 includes an operational amplifier OPb, a variable resistor circuit 63b, a plurality of field effect transistors FETb1, FETb2, FETb3, FETb4, FETb5, a plurality of resistor elements Rb1, Rb2, Rb3, a plurality of capacitors Cb1, Cb2, etc.

Of these, the operational amplifier OPb, the variable resistor circuit 63b, the plurality of resistor elements Rb1, Rb2, Rb3, the plurality of capacitors Cb1, Cb2 are the same as the operational amplifier OPa, the variable resistor circuit 63a, the plurality of resistor elements Ra1, Ra2, Ra3, and the plurality of capacitor Ca1, Ca2 provided in the forward direction energization section 55. Therefore, their descriptions are not repeated.

In the case where the second state is established on the basis of the setting of the digital signal control section 51, in the reverse direction energization section 57, the reference voltage Vref is applied to the variable resistor circuit 63b as a result of feedback control performed by the operational amplifier OPb.

In the reverse direction energization section 57, the field effect transistors FETb1 and FETb2 form a current mirror circuit, and the field effect transistors FETb3 and FETb4 form another current mirror circuit. The field effect transistors FETb1 and FETb2 are of the same size. Also, the field effect transistors FETb3 and FETb4 are of the same size.

Therefore, in the reverse direction energization section 57, a current determined by the reference voltage Vref and the electrical resistance of the variable resistor circuit 63b flows through the field effect transistor FETb1, and a current of the same magnitude also flows through the field effect transistor FETb2. Further, a current whose magnitude is the same as that of the current flowing through the field effect transistor FETb2 also flows through the field effect transistor FETb3, and a current whose magnitude is the same as that of the current flowing through the field effect transistor FETb3 also flows through the field effect transistor FETb4. The current flowing to the field effect transistor FETb4 in this manner is supplied to the pump cell 14 through the pump current terminal 61 as a pump current Ip of a direction toward the field effect transistor FETb4 (reverse direction).

Namely, in the case where the second state is established on the basis of the setting of the digital signal control section 51, the pump current Ip of the reverse direction is supplied to the pump cell 14 by the reverse direction energization section 57.

Meanwhile, in the case where the first state is established on the basis of the setting of the digital signal control section 51, the voltage applied to the variable resistor circuit 63b of the reverse direction energization section 57 as a result of feedback control performed by the operational amplifier OPb becomes 0 V, and no current flows through the variable resistor circuit 63b of the reverse direction energization section 57. Namely, in the case where the first state is established on the basis of the setting of the digital signal control section 51, the supply of the pump current Ip by the reverse direction energization section 57 is not performed.

As described above, the current DA conversion section 35 receives the DAC control signal S1, which includes the information (supply direction, current value) of the pump current Ip computed by the digital computation section 33, performs DA conversion on the basis of the received digital information, and supplies to the pump cell 14 the pump current determined on the basis of the DAC control signal S1.

Specifically, the current DA conversion section 35 sets the current value of the pump current Ip on the basis of the electrical resistance of the variable resistor circuit 63a, 63b and the reference voltage Vref supplied from the reference voltage generation section 41. Also, the current DA conversion section 35 sets the supply direction of the pump current Ip by selectively establishing the first or second state on the basis of the setting of the digital signal control section 51.

Notably, in the present embodiment, the field effect transistors which form each current mirror circuit are of the same size. However, current amplification may be performed by changing the dimensional ratio of the field effect transistors.

1-3. Maximum Current Range of Pump Current Ip

Now, there will be described the reason why the accuracy in controlling the pump current Ip can be improved by changing the maximum current range of the pump current Ip which the sensor control apparatus 2 can supply.

Figure 3:
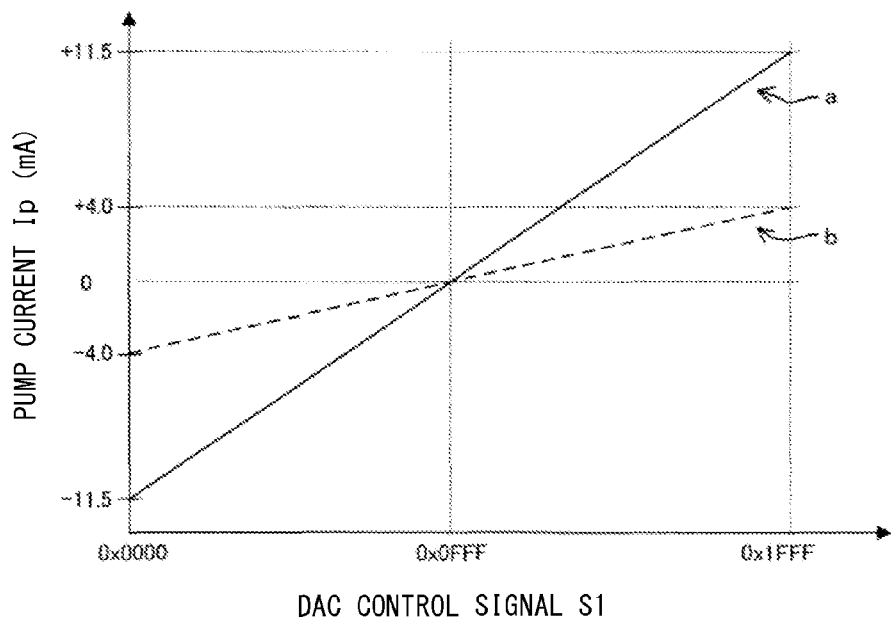
FIG. 3 is an explanatory graph showing the correlation between DAC control current S1 and pump current IP in the current DA conversion section 35.

FIG. 3 shows an explanatory graph representing the correlation between the pump current Ip and the DAC control signal S1 (13-bit data) in the current DA conversion section 35 of the sensor control apparatus 2.

Notably, in FIG. 3, a continuous line a shows the correlation in the case where the reference voltage Vref is set such that the maximum current range of the pump current Ip becomes "−11.5 mA to 11.5 mA," and a broken line b shows the correlation in the case where the reference voltage Vref is set such that the maximum current range of the pump current Ip becomes "−4.0 mA to 4.0 mA."

As can be understood from FIG. 3, when the DAC control signal S1 is greater than "0xOFFF," the pump current Ip becomes an energization current of the forward direction; when the DAC control signal S1 is less than "0xOFFF," the pump current Ip becomes an energization current of the reverse direction; and when the DAC control signal S1 is "0xOFFF," the pump current Ip is not supplied.

The current DA conversion section 35 generates a current corresponding to the maximum value of the maximum current range of the pump current Ip when the DAC control signal S1 is the maximum value "0x1FFF," and generates a current corresponding to the minimum value of the maximum current range of the pump current Ip when the DAC control signal S1 is the minimum value "0x0000."

Therefore, in the case where a sensor control apparatus 2 in which the maximum current range of the pump current Ip is set to the range of "−11.5 mA to 11.5 mA" is used so as to control a gas sensor whose maximum pump current (sensor maximum current value) is 4.0 mA, the magnitude of the pump current Ip corresponding to an increment of the DAC control signal S1 per bit (resolution) becomes 2.8 µA.

In contrast, in the case where a sensor control apparatus 2 in which the maximum current range of the pump current Ip is set to the range of "−4.0 mA to 4.0 mA" is used so as to control the gas sensor whose maximum pump current (sensor maximum current value) is 4.0 mA, the magnitude of the pump current Ip corresponding to an increment of the DAC control signal S1 per bit (resolution) becomes 0.98 µA.

Namely, in the case where the upper limit value of the maximum current range of the pump current Ip which the sensor control apparatus 2 can supply is set to a value greater than the sensor maximum current value of the gas sensor, the magnitude of the pump current Ip corresponding to an increment of the DAC control signal S1 per bit (resolution) increases, and the accuracy in controlling the pump current Ip decreases.

In contrast, in the case where the maximum current range of the pump current Ip which the sensor control apparatus 2 can supply is narrowed as much as possible in accordance with the sensor maximum current value of the gas sensor, the magnitude of the pump current Ip corresponding to an increment of the DAC control signal S1 per bit (resolution) can be decreased, and the accuracy in controlling the pump current Ip can be increased.

The sensor control apparatus 2 of the present embodiment can control gas sensors of various types or gas sensors having various characteristics by properly setting, in advance, the information stored in the EEPROM 37 (information which is a portion of the sensor information and relates to the reference voltage Vref corresponding to the maximum current range of the pump current Ip) in accordance with the type or characteristic of each gas sensor 8.

1-4. Deterioration Correction Process

Next, there will be described a deterioration correction process executed by the engine control apparatus 9.

Notably, the deterioration correction process is performed so as to rewrite the "information regarding the reference voltage Vref" which is a portion of the sensor information stored in the EEPROM 37 and the RAM 39 in accordance with the degree of degradation of the gas sensor 8 caused by the influence of a change with time or the like.

The deterioration correction process is performed, for example, when the engine control apparatus 9 receives a correction instruction signal from an external device. Notably, the correction instruction signal is sent to the engine control apparatus 9 in a state in which the atmosphere of the gas under measurement satisfies a predetermined deterioration correction execution condition (in the present embodiment, the oxygen concentration=16 vol %, the atmospheric pressure=100 kPa, after activation of the gas sensor) (specifically, in a fuel cut state).

Figure 4:
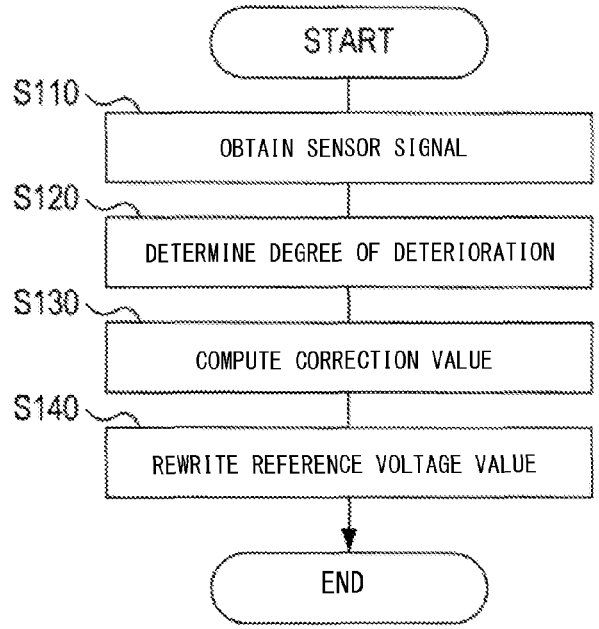
FIG. 4 is a flowchart showing the details of deterioration correction processing.

FIG. 4 shows a flowchart representing the details of the deterioration correction process.

When the deterioration correction process is started, in S110 (S stands for "step"), the engine control apparatus 9 obtains the result (the DAC control signal S1) of computation in the pump current control process executed by the digital computation section 33. The engine control apparatus 9 obtains the DAC control signal S1 from the digital computation section 33 via the SPI control section 43 and the SPI communication line 44. Namely, in S110, the engine control apparatus 9 obtains from the digital computation section 33 the result (the DAC control signal S1) of computation in the pump current control process under an environment which satisfies the deterioration correction execution condition.

Next, in S120, the engine control apparatus 9 calculates the difference (deviation) between a deterioration determination reference value set in advance and a pump current Ip reduced value calculated from the DAC control signal S1 obtained in S110. The engine control apparatus 9 then computes a detection error of the gas sensor 8 by using the deviation and a predetermined map or computation formula, and determines the degree of deterioration of the gas sensor 8. Notably, in S120, the engine control apparatus 9 also performs a process of calculating the pump current Ip reduced value on the basis of the DAC control signal S1.

For example, in the case where the pump current Ip reduced value is "2.87 mA" and the deterioration determination reference value set in advance is "2.90 mA," the deviation becomes "−0.03 mA." The engine control apparatus 9 computes the detection error (e.g., −1.0%) of the gas sensor 8 by using the deviation and the predetermined map (or computation formula).

Since the detection error of the gas sensor 8 changes with the degree of deterioration of the gas sensor 8 itself, the detection error, which is the result of the computation in S120, represents the degree of deterioration of the gas sensor 8.

Next, in S130, the engine control apparatus 9 computes, on the basis of the result of the computation in S120, a correction value of the "information regarding the reference voltage Vref." Specifically, the engine control apparatus 9 computes the correction value of the "information regarding the reference voltage Vref" by using the result of the computation in S120 (the detection error of the gas sensor 8) and a predetermined map or computation formula.

Next, in S140, the engine control apparatus 9 transmits via the SPI communication line 44 to the sensor control apparatus 2 the correction value of the "information regarding the reference voltage Vref" (for example, 2.7 V) computed in S130.

Upon receipt of the correction value of the "information regarding the reference voltage Vref," the SPI control section 43 performs a process of writing (overwriting) the correction value of the "information regarding the reference voltage Vref" in the RAM 39 as the "information regarding the reference voltage Vref." As a result, the reference voltage Vref supplied from the reference voltage generation section 41 to the current DA conversion section 35 is changed, whereby the maximum current range of the pump current Ip which the current DA conversion section 35 can supply, and the magnitude of the pump current Ip corresponding to the increment of the DAC control signal S1 per bit (resolution) are changed to a proper range and a proper value, respectively, which correspond to the degree of deterioration of the gas sensor 8.

1-5. Effects

As described above, in the gas detection system 1 of the present embodiment, the sensor control apparatus 2 includes the reference voltage generation section 41 and can change the maximum current range of the pump current Ip in the current DA conversion section 35.

The sensor control apparatus 2 having such a configuration can change the maximum current range of the pump current Ip to a proper range in accordance with the type or characteristic of a gas sensor 8 to be controlled.

Namely, in the case where a gas sensor 8 whose sensor maximum current is small is controlled, the maximum current range of the current DA conversion section 35 is changed to a range determined in consideration of the sensor maximum current of the gas sensor 8, whereby the accuracy in controlling the pump current Ip is restrained from decreasing.

Therefore, according to the gas detection system 1 of the present embodiment, when the gas sensor is controlled by means of digital control, a decrease in the accuracy in controlling the pump current Ip can be restrained.

Also, the current DA conversion section 35 provided in the sensor control apparatus 2 is configured such that the maximum current range of the pump current Ip changes with the reference voltage Vref supplied from the reference voltage generation section 41. Therefore, the maximum current range of the pump current Ip supplied from the current DA conversion section 35 to the pump cell 14 of the gas sensor 8 can be changed freely by changing the reference voltage Vref generated by the reference voltage generation section 41.

Also, the current DA conversion section 35 includes the variable resistor circuits 63a and 63b whose electrical resistances change with the DAC control signal S1 from the digital computation section 33, and is configured to supply to the pump cell 14, as the pump current Ip, a current produced as a result of application of the reference voltage Vref to the variable resistor circuits 63a and 63b.

Namely, since the current DA conversion section 35 includes the variable resistor circuits 63a and 63b, the current DA conversion section 35 can change its electrical characteristic (electrical resistance) in accordance with the computation result (the DAC control signal S1) of the pump current control process performed by the digital computation section 33. Since the pump current Ip is a current produced as a result of application of the reference voltage Vref to the variable resistor circuits 63a and 63b, the pump current Ip can assume an arbitrary value corresponding to the result of the computation by the digital computation section 33.

As a result, the current DA conversion section 35 can supply to the pump cell 14 the pump current Ip corresponding to the result of the computation by the digital computation section 33.

In the sensor control apparatus 2, the EEPROM 37 stores sensor information which includes information regarding the reference voltage Vref corresponding to the maximum current range of the pump current Ip. This sensor information is determined in accordance with the type or characteristic of the gas sensor 8 to be controlled, and is stored in the EEPROM 37 during manufacture of the sensor control apparatus 2.

Since the information regarding the reference voltage Vref is determined in accordance with the type or characteristic of the gas sensor 8 and is stored in the EEPROM 37, the sensor control apparatus 2 can set a proper maximum current range of the pump current Ip in accordance with the type or characteristic of the gas sensor 8.

Also, through employment of the configuration in which the sensor information which includes the information regarding the reference voltage Vref is stored in the EEPROM 37, the information stored in the EEPROM 37 (the sensor information including the information regarding the reference voltage Vref) can be changed in accordance with the gas sensor 8 to be controlled.

As a result, the sensor control apparatus 2 of the present invention can cope with gas sensors of various types or gas sensors having various characteristics, and can restrain a decrease in the accuracy in controlling the pump current Ip.

1-6. Correspondence to Claims

Here, there will be described the correspondence between the claims and the present embodiment in terms of wording.

Exhaust gas discharged from the internal combustion engine corresponds to the gas under measurement, oxygen corresponds to the specific gas, the pump cell 14 corresponds to the oxygen pump cell, and the electromotive force cell 24 corresponds to the detection cell.

Also, the digital computation section 33 corresponds to the pump current computation section, the current DA conversion section 35 corresponds to the digital-to-analog conversion section, the reference voltage generation section 41 corresponds to the maximum current range change section, the variable resistor circuits 63a and 63b correspond to the variable resistance section, the EEPROM 37 and the RAM 39 correspond to the storage section, the "information regarding the reference voltage Vref" corresponds to the sensor information, and the AD conversion section 31 corresponds to the analog-to-digital conversion section.

2. Second Embodiment

As a second embodiment, there will be described a second gas detection system 101 including a second sensor control apparatus 102 in which the EEPROM 37 stores a plurality of pieces of information each relating to the maximum current range of the pump current Ip and corresponding to a plurality of types of gas sensors and which controls the pump current by using one piece of information selected from the plurality of pieces of information.

Notably, in the following description, of the constituent elements of the second embodiment, constituent elements identical with those of the first embodiment are denoted by the same reference numerals as those used in the first embodiment, and their descriptions are omitted. Of the constituent elements of the second embodiment, constituent elements different from those of the first embodiment will be mainly described.

Figure 5:
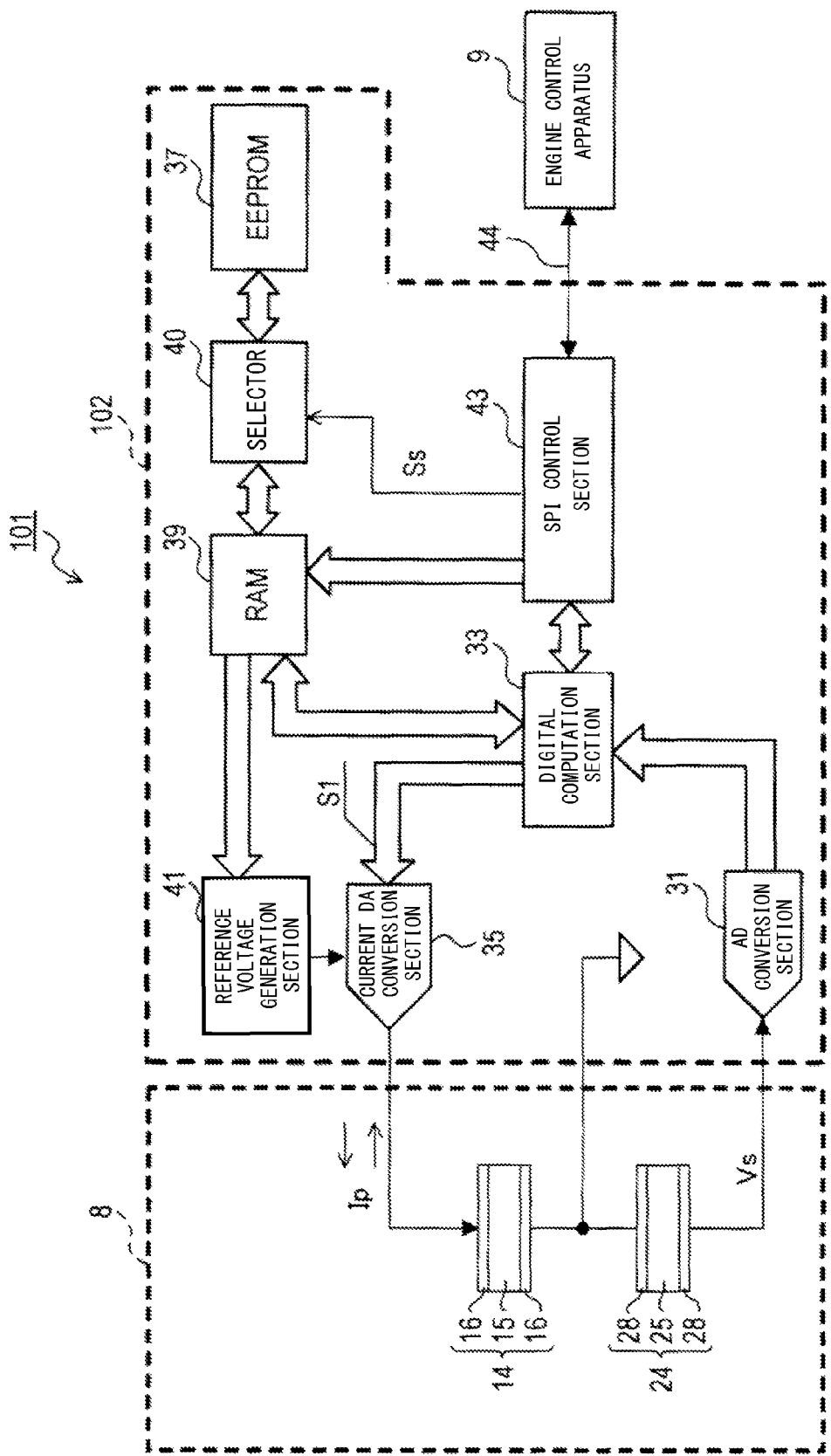
FIG. 5 is an overall diagram of a second gas detection system 101 of a second embodiment.

FIG. 5 is an overall diagram of the second gas detection system 101 of the second embodiment.

The second sensor control apparatus 102 of the second embodiment is configured by adding a selector section 40 to the sensor control apparatus 2 of the first embodiment.

The EEPROM 37 stores a plurality of pieces of information which correspond to a plurality of types of gas sensors and each of which relates to the reference voltage Vref corresponding to the maximum current range of the pump current Ip. For example, in the case where the EEPROM 37 stores two pieces of information regarding gas sensors of two types (types A and B), the EEPROM 37 stores a piece of information (3.0 V) regarding the reference voltage Vref of the gas sensor of the type A, and a piece of information (1.0 V) regarding the reference voltage Vref of the gas sensor of the type B.

The selector section 40 is provided between the EEPROM 37 and the RAM 39, and performs a process of selecting various types of pieces of information transmitted and received between the EEPROM 37 and the RAM 39 on the basis of an externally provided selection instruction.

Namely, on the basis of a sensor type signal Ss received from the engine control apparatus 9 via the SPI control section 43 and the SPI communication line 44, the selector section 40 selects one piece of information from the plurality of pieces of information stored in the EEPROM 37 and writes the selected piece of information into the RAM 39. For example, in the case where the content of the sensor type signal Ss is an "instruction instructing selection of the type A," the selector 40 reads out the "piece of information (3.0 V) regarding the reference voltage Vref of the gas sensor of the type A" from the EEPROM 37 as the information regarding the reference voltage Vref, and writes that information in the RAM 39.

The reference voltage generation section 41 generates the reference voltage Vref on the basis of the "information regarding the reference voltage Vref" temporarily stored in the RAM 39 on the basis of the senor type signal Ss, and supplies the generated reference voltage Vref to the current DA conversion section 35.

The current DA conversion section 35 sets the maximum current range of the pump current Ip on the basis of the reference voltage Vref.

The second sensor control apparatus 102 having the above-described configuration can eliminate the necessity of restricting the type of the gas sensor 8 to one type in the manufacturing stage, and can set the maximum current range of the pump current Ip corresponding to the type of the gas sensor 8 in the stage of actual use by receiving a selection instruction (the sensor type signal Ss) from the engine control apparatus 9.

Notably, the engine control apparatus 9 is configured such that the type of the gas sensor 8 can be input to the engine control apparatus 9 and is configured to transmit the selection instruction (the sensor type signal Ss) in accordance with the input type.

Therefore, according to the second sensor control apparatus 102 and the second gas detection system 101 of the second embodiment, the maximum current range of the pump current Ip corresponding to the type of the gas sensor 8 can be set on the basis of the selection instruction (the sensor type signal Ss) from the engine control apparatus 9. Therefore, the accuracy in controlling the pump current Ip can be restrained from decreasing.

3. Third Embodiment

As a third embodiment, there will be described a third gas detection system which is configured by replacing the current DA conversion section 35 of the gas detection system 1 of the first embodiment with a second current DA conversion section 135.

Notably, in the following description, of the constituent elements of the third embodiment, constituent elements identical with those of the first embodiment are denoted by the same reference numerals as those used in the first embodiment, and their descriptions are omitted. Of the constituent elements of the third embodiment, constituent elements different from those of the first embodiment will be mainly described.

The second current DA conversion section 135 is configured by replacing the forward direction energization section 55 of the current DA conversion section 35 of the first embodiment shown in FIG. 2 with a second forward direction energization section 155, and by replacing the reverse direction energization section 57 thereof with a second reverse direction energization section 157.

Figure 6:
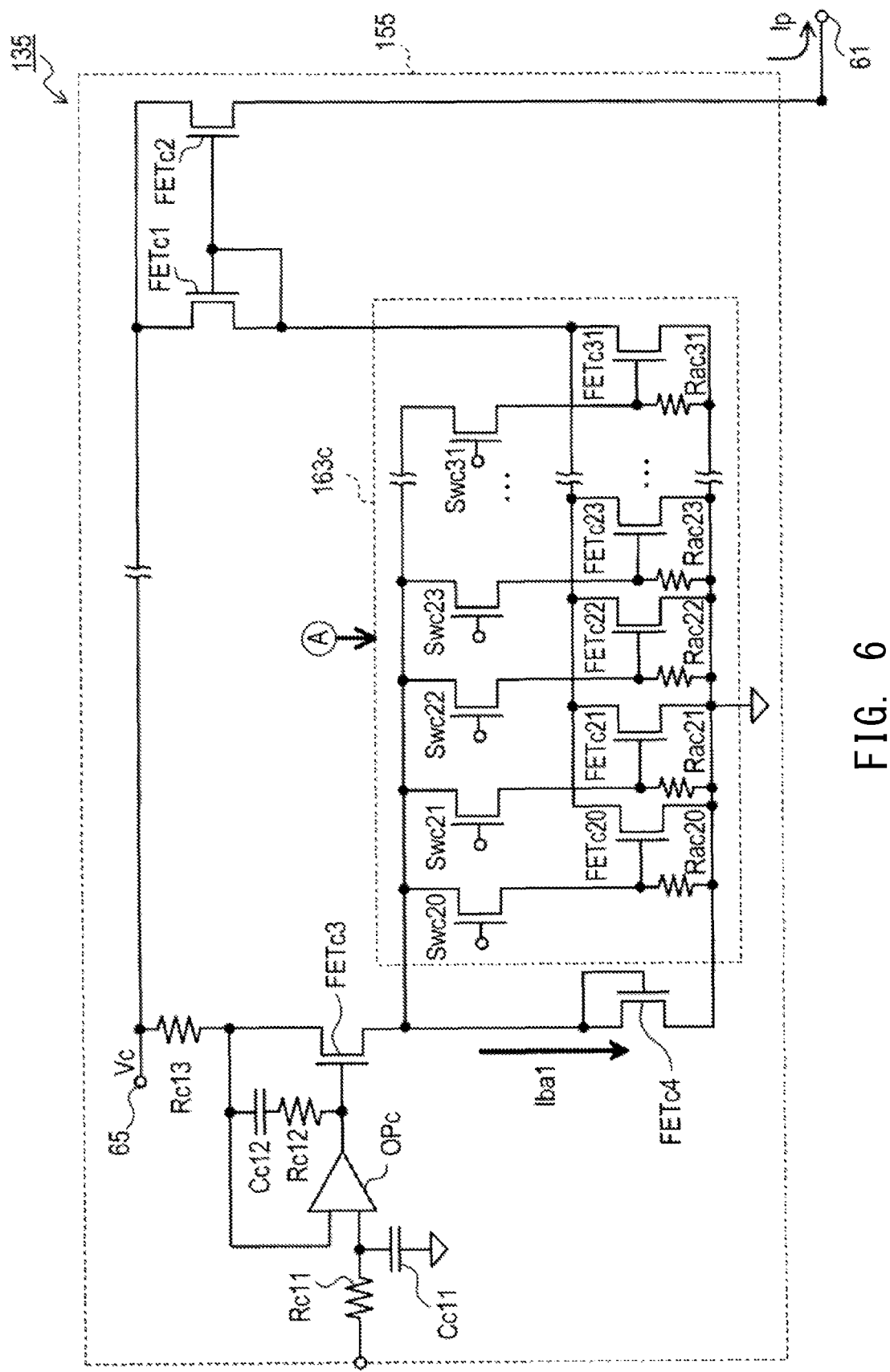
FIG. 6 is an overall diagram of a second forward direction energization section 155 provided in a second current DA conversion section 135.
Figure 7:
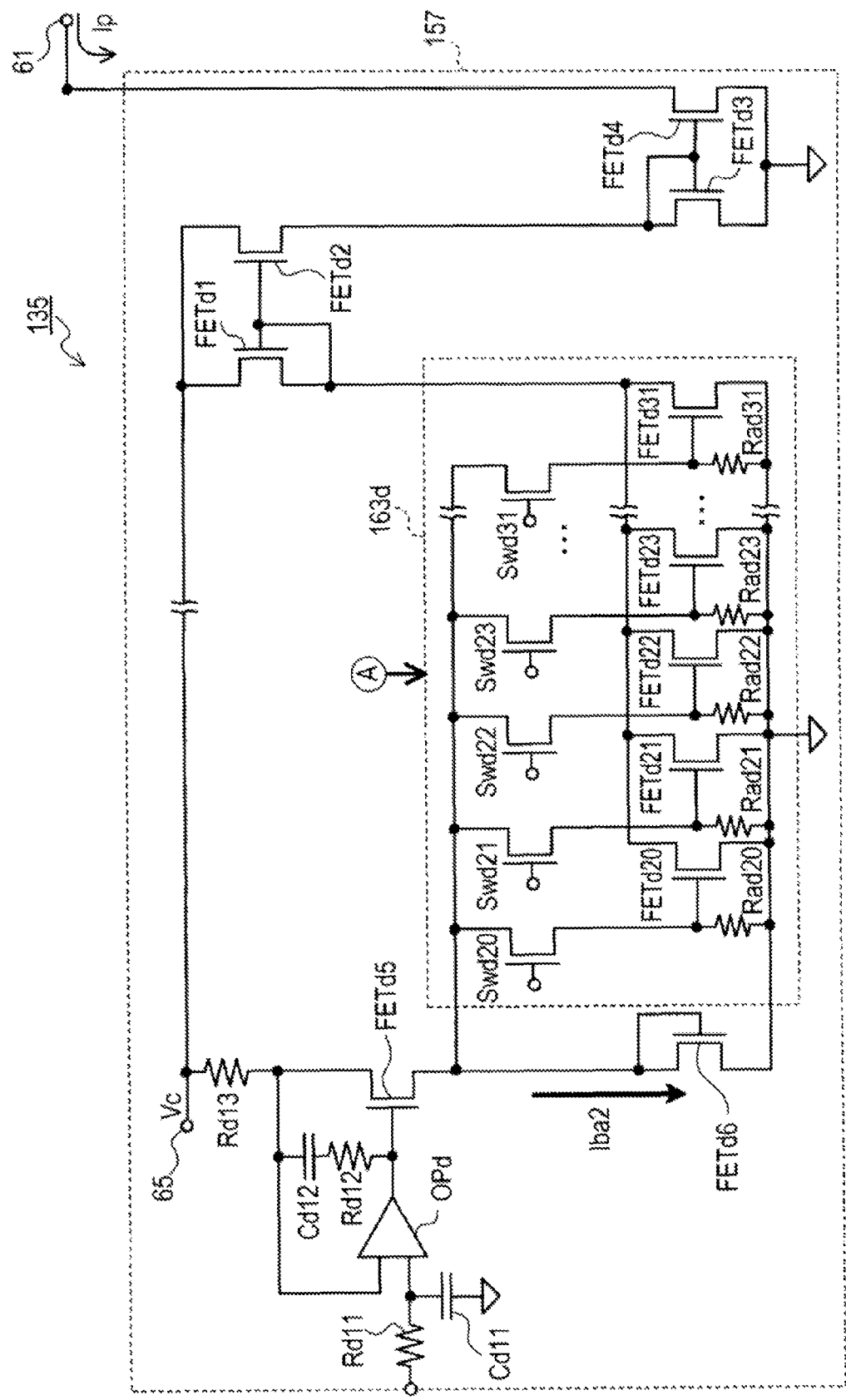
FIG. 7 is an overall diagram of a second reverse direction energization section 157 provided in the second current DA conversion section 135.

FIG. 6 is an overall diagram of the second forward direction energization section 155 provided in the second current DA conversion section 135, and FIG. 7 is an overall diagram of the second reverse direction energization section 157 provided in the second current DA conversion section 135.

As shown in FIG. 6, the second forward direction energization section 155 includes an operational amplifier OPc, a variable current circuit 163c, a plurality of field effect transistors FETc1, FETc2, FETc3, FETc4, a plurality of resistor elements Rc11, Rc12, Rc13, a plurality of capacitors Cc11, Cc12, etc.

When the above-described first state is established on the basis of the setting of the digital signal control section 51, in second forward direction energization section 155, a reference current Iba1 is generated as a result of feedback control performed by the operational amplifier OPc. Notably, the reference current Iba1 is a current flowing from the field effect transistor FETc3 toward the field effect transistor FETc4, and the relation "the reference current Iba1=the reference voltage Vref/(the resistance of the resistor element Rc13)" stands. Namely, the magnitude of the reference current Iba1 changes with the reference voltage Vref.

The variable current circuit 163c includes 12 field effect transistors FETc20 to FETc31, 12 resistor elements Rac20 to Rac31, and 12 switching elements Swc20 to Swc31. In FIG. 6, some of the field effect transistors FETc20 to FETc31, some of the resistor elements Rac20 to Rac31, and some of the switching elements Swc20 to Swc31 are not shown.

Although the field effect transistors FETc20 to FETc31 have the same gate length, they have different gate widths. The gate widths of the field effect transistors FETc20 to FETc31 are determined such that the ratio of the gate width of the nth field effect transistor to a reference gate width W becomes "the nth power of 2." For example, in the case where the gate width of the field effect transistor FETc20 is "W×(the 0th power of 2)," the gate width of the field effect transistor FETc21 is "W×(the 1st power of 2), the gate width of the field effect transistor FETc22 is "W×(the 2nd power of 2), and the gate width of the field effect transistor FETc31 is "W×(the 11th power of 2). Notably, a drain current in proportion to the gate width of a field effect transistor flows through the field effect transistor.

When the switching elements Swc20 to Swc31 corresponding to the field effect transistors FETc20 to FETc31 are each brought into the closed state (ON state), the same gate voltage as the gate voltage of the field effect transistor FETc4 is applied to the field effect transistors FETc20 to FETc31. Therefore, drain currents which are proportional to the reference current Iba1 and are proportional to the respective gate widths flow through the field effect transistors FETc20 to FETc31, respectively.

The states (open (OFF) states or closed (ON) states) of the 12 switching elements Swc20 to Swc31 are set on the basis of the DAC control signal S1. Namely the variable resistor circuit 163c is configured to change the current which the field effect transistors FETc20 to FETc31 can supply as a whole, on the basis of the DAC control signal S1 (specifically, information regarding the current value). The sum of the currents flowing through the field effect transistors FETc20 to FETc31 becomes equal to the current flowing through the field effect transistors FETc1.

Notably, in order to reduce the influence of the voltage drops at the field effect transistors FETc20 to FETc31 in the ON state on the control resolution of the current flowing through the field effect transistor FETc1, the resistances of the resistor elements Rac20 to Rac31 are made larger than those of the switching elements Swc20 to Swc31 in the ON state.

By virtue of the above-described configuration, when the above-described first state is established on the basis of the setting of the digital signal control section 51, in the second forward direction energization section 155, the reference current Iba1 determined in accordance with the reference voltage Vref is supplied to the field effect transistor FETc4. In the variable current circuit 163c, currents which are in proportional to the reference current Iba1 and are determined on the basis of the DAC control signal S1 (superficially, information regarding the current value) flow through the field effect transistors FETc20 to FETc31, respectively, and flow through the field effect transistor FETc1.

Namely, when the above-described first state is established on the basis of the setting of the digital signal control section 51, in the second forward direction energization section 155, a current determined in accordance with the reference voltage Vref and the DAC control signal S1 flows through the field effect transistor FETc1.

Also, in the second forward direction energization section 155, the field effect transistors FETc1 and FETc2 form a current mirror circuit, and the two field effect transistors are of the same size in the present embodiment. Therefore, a current of the same magnitude as that of the current flowing through the field effect transistor FETc1 also flows through the field effect transistor FETc2. The current flowing through the field effect transistor FETc2 in this manner is supplied to the pump cell 14 through the pump current terminal 61 as a pump current Ip of a direction toward the pump cell 14 (forward direction).

Namely, in the case where the above-described first state is established on the basis of the setting of the digital signal control section 51, the pump current Ip of the forward direction is supplied to the pump cell 14 by the second forward direction energization section 155.

Meanwhile, in the case where the above-described second state is established on the basis of the setting of the digital signal control section 51, the reference current Iba1 generated as a result of feedback control performed by the operation amplifier OPc becomes 0 A; i.e., a state in which the reference current Iba1 is not generated is established. Namely, in the case where the reference voltage Vref is not supplied to the second forward direction energization section 155, the supply of the pump current Ip by the second forward direction energization section 155 is not performed.

As shown in FIG. 7, the second reverse direction energization section 157 includes an operational amplifier OPd, a variable current circuit 163d, a plurality of field effect transistors FETd1, FETd2, FETd3, FETd4, FETd5, FETd6, a plurality of resistor elements Rd11, Rd12, Rd13, a plurality of capacitors Cd11, Cd12, etc.

Of these components, the operational amplifier OPd, the variable current circuit 163d, the plurality of resistor elements Rd11, Rd12, Rd13, and the plurality of capacitors Cd11, Cd12 are the same as the operational amplifier OPc, the variable current circuit 163c, the plurality of resistor elements Rc11, Rc12, Rc13, and the plurality of capacitors Cc11, Cc12 which are provided in the second forward direction energization section 155. Therefore, their descriptions are omitted.

When the above-described second state is established on the basis of the setting of the digital signal control section 51, in second reverse direction energization section 157, a second reference current Iba2 is generated as a result of feedback control performed by the operational amplifier OPd. Notably, the second reference current Iba2 is a current flowing from the field effect transistor FETd5 toward the field effect transistor FETd6, and the relation "the second reference current Iba2=the reference voltage Vref/(the resistance of the resistor element Rd13)" stands. Namely, the current value of the second reference current Iba2 changes with the reference voltage Vref.

In the variable current circuit 163d, currents which are in proportional to the second reference current Iba2 and are determined on the basis of the DAC control signal S1 (superficially, information regarding the current value) flow through the field effect transistors FETd20 to FETd31, respectively, and flow through the field effect transistor FETd1.

Namely, when the above-described second state is established on the basis of the setting of the digital signal control section 51, in the second reverse direction energization section 157, a current determined in accordance with the reference voltage Vref and the DAC control signal S1 flows through the field effect transistor FETd1.

Also, in the second reverse direction energization section 157, the field effect transistors FETd1 and FETd2 form a current mirror circuit, and the field effect transistors FETd3 and FETd4 form another current mirror circuit. The field effect transistors FETd1 and FETd2 are of the same size, and the field effect transistors FETd3 and FETd4 are of the same size.

Therefore, in the second reverse direction energization section 157, a current determined in accordance with the reference voltage Vref and the DAC control signal S1 flows through the field effect transistor FETd1, and a current of the same magnitude also flows through the field effect transistor FETd2. Further, a current whose magnitude is the same as that of the current flowing through the field effect transistor FETd2 also flows through the field effect transistor FETd3, and a current whose magnitude is the same as that of the current flowing through the field effect transistor FETd3 also flows through the field effect transistor FETd4. The current flowing through the field effect transistor FETd4 in this manner is supplied to the pump cell 14 through the pump current terminal 61 as a pump current Ip of a direction toward the field effect transistor FETd4 (reverse direction).

Namely, in the case where the above-described second state is established on the basis of the setting of the digital signal control section 51, the pump current Ip of the reverse direction is supplied to the pump cell 14 by the second reverse direction energization section 157.

Meanwhile, in the case where the above-described first state is established on the basis of the setting of the digital signal control section 51, the second reference current Iba2 generated as a result of feedback control performed by the operational amplifier OPd becomes 0 A; i.e., a state in which the second reference current Iba2 is not generated is established. Namely, in the case where the reference voltage Vref is not supplied to the second reverse direction energization section 157, the supply of the pump current Ip by the second reverse direction energization section 157 is not performed.

As described above, the second current DA conversion section 135 receives the DAC control signal S1, which includes the information (supply direction, current value) of the pump current Ip computed by the digital computation section 33, performs DA conversion on the basis of the received digital information, and supplies to the pump cell 14 the pump current determined on the basis of the DAC control signal S1.

Specifically, the second current DA conversion section 135 sets the current value of the pump current Ip on the basis of the reference voltage Vref supplied from the reference voltage generation section 41 and the DAC control signal S1 from the digital computation section 33. Also, the second current DA conversion section 135 sets the supply direction of the pump current Ip by selectively establishing the first or second state on the basis of the setting of the digital signal control section 51.

The second current DA conversion section 135 having such a configuration can be used in place of the current DA conversion section 35 of the first embodiment.

Here, there will be described the correspondence between the claims and the present embodiment in terms of wording.

The second current DA conversion section 135 corresponds to the digital-to-analog conversion section.

4. Other Embodiments

The embodiments of the present invention have been described above; however, the present invention is not limited to the above-described embodiments and can be practiced in various forms without departing from the scope of the present invention.

For example, in the above-described embodiments, a data communication method using a serial peripheral interface is employed for communications between the sensor control apparatus and the engine control apparatus. However, other data communication methods may be employed. For example, CAN communications (Controller Area Network communications) may be employed.

Figure 8:
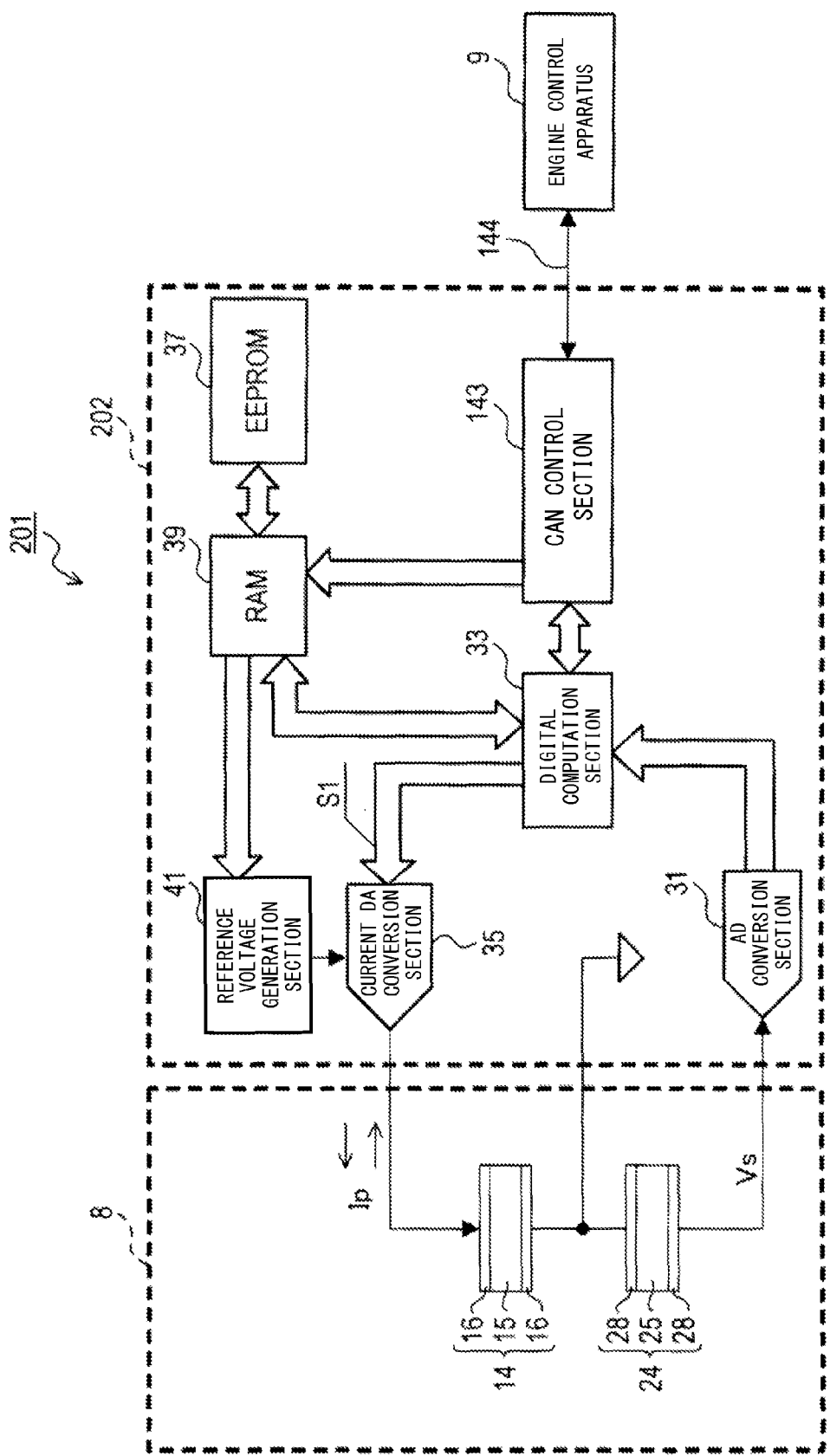
FIG. 8 is an overall diagram of a fourth gas detection system 201 of a fourth embodiment.

FIG. 8 shows the overall diagram of a fourth gas detection system 201 of a fourth embodiment configured by replacing the SPI control section 43 and the SPI communication line 44 in the gas detection system 1 of the first embodiment with a CAN control section 143 and a CAN communication line 144, respectively. Notably, the sensor control apparatus provided in the fourth gas detection system 201 of the fourth embodiment is a fourth sensor control apparatus 202.

Figure 9:
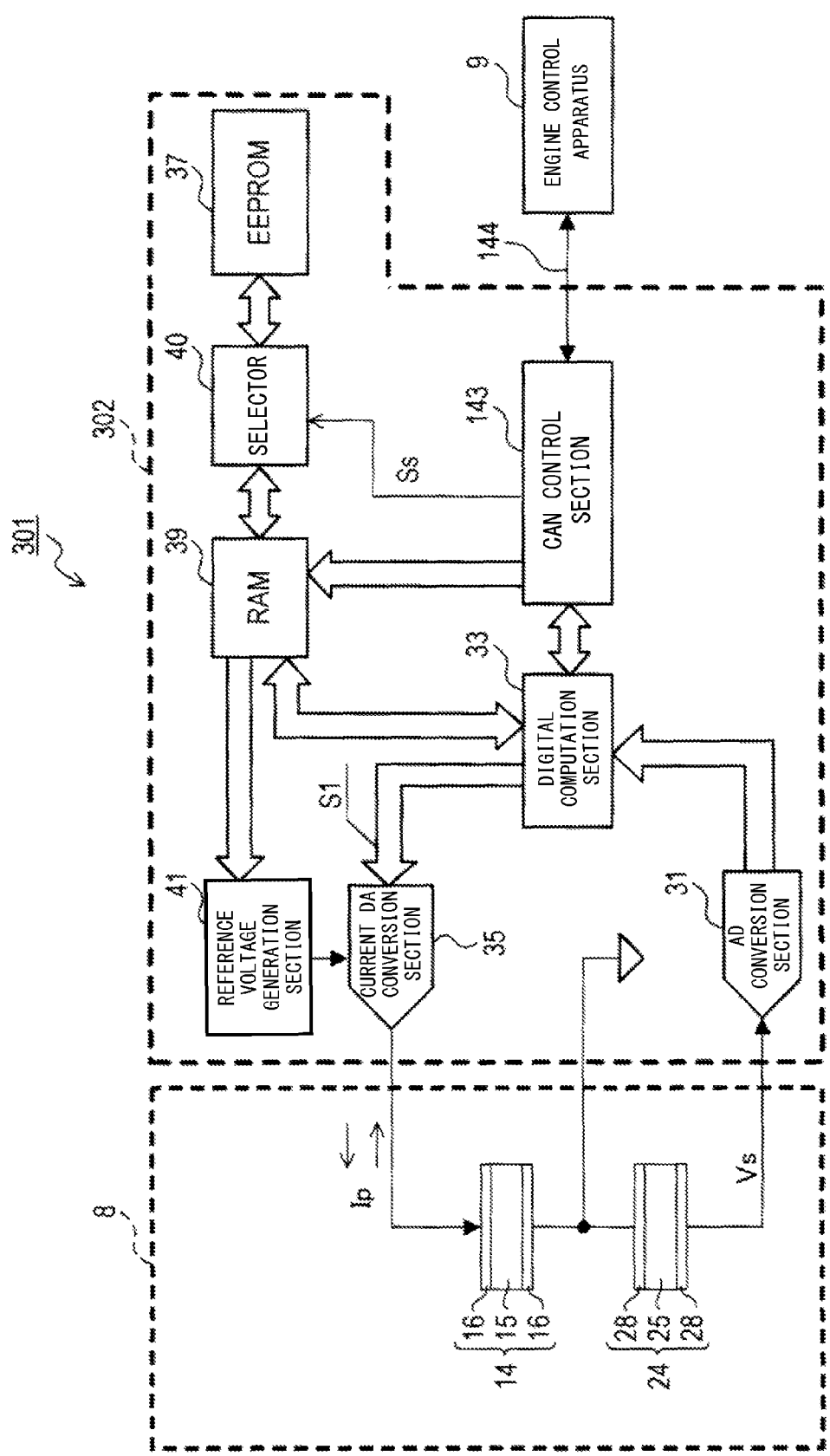
FIG. 9 is an overall diagram of a fifth gas detection system 301 of a fifth embodiment.
Figure 10:
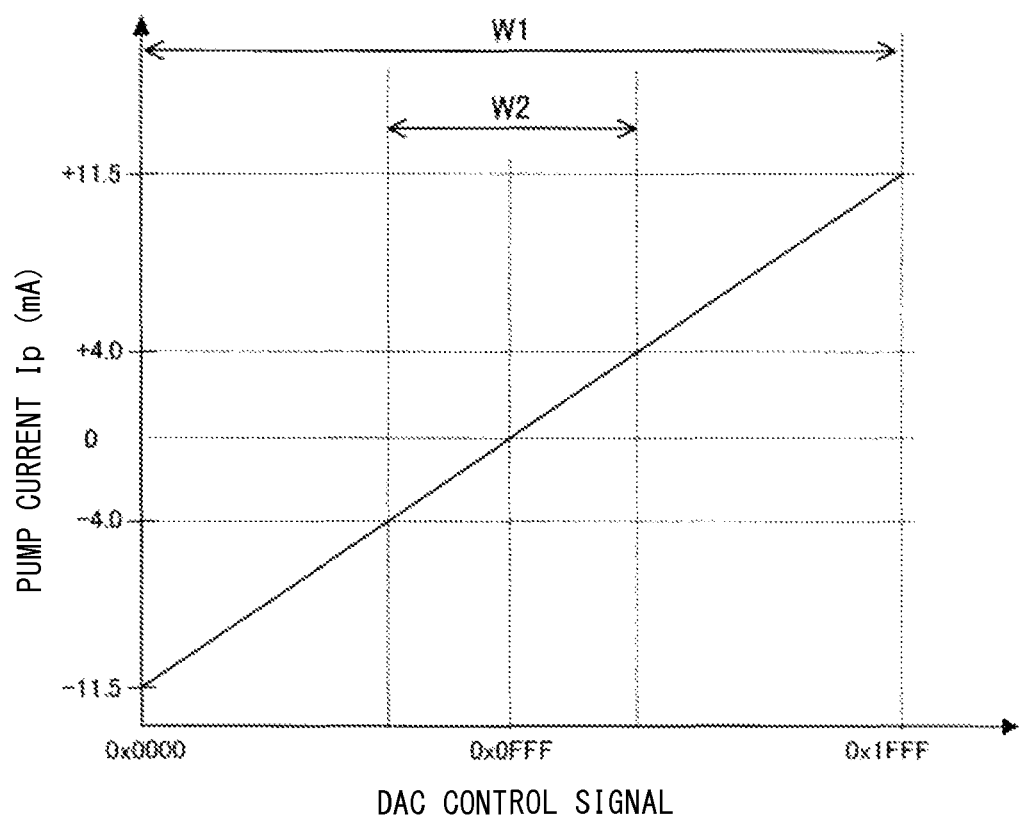
FIG. 10 is an explanatory graph showing the characteristic of a digital-to-analog conversion section (current DAC).

FIG. 9 shows the overall diagram of a fifth gas detection system 301 of a fifth embodiment configured by replacing the SPI control section 43 and the SPI communication line 44 in the second gas detection system 101 of the second embodiment with a CAN control section 143 and a CAN communication line 144, respectively. Notably, the sensor control apparatus provided in the fifth gas detection system 301 of the fifth embodiment is a fifth sensor control apparatus 302.

As in the first and second embodiments, the fourth gas detection system 201 and the fifth gas detection system 301 can restrain a decrease in the accuracy in controlling the pump current Ip when the gas sensor is controlled by means of digital control.

The gas sensor is not limited to gas sensors for detecting oxygen, and may be other types of sensors including an oxygen pump cell for performing pumping in or pumping out of oxygen, for example, an NOx sensor for detecting NOx. Also, the gas sensor may be a gas sensor which does not include any electromotive force cell (detection cell) and which detects oxygen by an oxygen pump cell only.

The reference voltage generation section 41 may read from the RAM 39 "information regarding the sensor maximum current of the pump cell" or "information regarding the maximum current range of the pump current Ip corresponding to the sensor maximum current" instead of the "information regarding the reference voltage Vref," compute the reference voltage Vref by computation processing based on that information, and generate the reference voltage Vref on the basis of the result of the computation.

The second embodiment is configured to store in the EEPROM 37 a plurality of pieces of information which correspond to a plurality of types of gas sensors and which relate to the reference voltage Vref corresponding to the maximum current range of the pump current Ip. However, the plurality of pieces of information are not limited to "information regarding a plurality of types of gas sensors." For example, the second embodiment may be configured to store in the EEPROM 37, as a plurality of pieces of information, "information regarding the degrees of deterioration of gas sensors of the same type" or "information regarding the individual differences of gas sensors of the same type."

Namely, in the case where the "information regarding the degrees of deterioration of gas sensors of the same type" is stored as the plurality of pieces of information, by changing the reference voltage Vref in accordance with the degree of deterioration of each gas sensor, the maximum current range of the pump current Ip can be set to a range corresponding to the degree of deterioration of the gas sensor. As a result, even in an application in which gas detection is performed over a long period of time, a decrease in the accuracy in controlling the pump current Ip caused by the deterioration of the gas sensor can be restrained.

Also, in the case where the "information regarding the individual differences of gas sensors of the same type" is stored as the plurality of pieces of information, by changing the reference voltage Vref in accordance with the individual difference of each gas sensor, the maximum current range of the pump current Ip can be set to a range corresponding to the individual difference of the gas sensor. As a result, even in the case where the characteristics of gas sensors vary due to the individual differences thereof, a decrease in the accuracy in controlling the pump current Ip caused by the individual difference of each gas sensor can be restrained.

DESCRIPTION OF REFERENCE NUMERALS

1 . . . gas detection system,
2 . . . sensor control apparatus,
8 . . . gas sensor (oxygen sensor),
9 . . . engine control apparatus,
14 . . . pump cell,
24 . . . electromotive force cell,
31 . . . AD conversion section (analog-to-digital conversion section),
33 . . . digital computation section,
35 . . . current DA conversion section (current digital-to-analog conversion section),
37 . . . EEPROM,
39 . . . RAM,
40 . . . selector section,
41 . . . reference voltage generation section,
63a, 63b . . . variable resistor circuit,
101 . . . second gas detection system,
102 . . . second sensor control apparatus,
135 . . . second current DA conversion section,
163c, 163d . . . variable current circuit,
201 . . . fourth gas detection system,
202 . . . fourth sensor control apparatus,
301 . . . fifth gas detection system,
302 . . . fifth sensor control apparatus.

What is claimed is:

1. A sensor control apparatus which controls a gas sensor having an oxygen pump cell for pumping oxygen in or out in accordance with a pump current, comprising:

a pump current computation section which computes a digital signal corresponding to a pump current supplied to the oxygen pump cell, and provides the digital signal;

a digital-to-analog conversion section which generates the pump current on the basis of the digital signal; and a maximum current range change section which changes a maximum current range of the pump current which can be generated by the digital-to-analog conversion section.

2. A sensor control apparatus according to claim 1, wherein the maximum current range change section generates a reference voltage; and the digital-to-analog conversion section is configured such that the maximum current range changes with the reference voltage.

3. A sensor control apparatus according to claim 2, wherein the digital-to-analog conversion section includes a variable resistance section having variable electrical resistance, and generates, as the pump current, a current produced as a result of application of the reference voltage to the variable resistance section.

4. A sensor control apparatus according to claim 1, further comprising a storage section for storing sensor information determined in accordance with a characteristic or type of the gas sensor, wherein the maximum current range change section changes the maximum current range on the basis of the sensor information.

5. A sensor control apparatus according to claim 1, wherein the gas sensor includes a detection cell which generates an electromotive force corresponding to a specific component contained in a gas under measurement;

the sensor control apparatus comprises an analog-to-digital conversion section for converting an analog value of the electromotive force to a digital value; and the pump current computation section computes the pump current on the basis of the digital value of the electromotive force.

6. A gas detection system comprising the sensor control apparatus according to claim 1 and a gas sensor having an oxygen pump cell for pumping oxygen in or out in accordance with pump current.

* * * * *